United States Patent [19]

Colarow

[11] Patent Number: 5,284,941
[45] Date of Patent: Feb. 8, 1994

[54] PROCESS FOR OBTAINING GLYCOLIPIDS AND PHOSPHOLIPIDS

[75] Inventor: Ladislas Colarow, Lausanne, Switzerland

[73] Assignee: Nestec S.A., Vevey, Switzerland

[21] Appl. No.: 415,629

[22] Filed: Oct. 2, 1989

[30] Foreign Application Priority Data

Oct. 28, 1988 [CH] Switzerland .......................... 4033/88

[51] Int. Cl.$^5$ .................. C07H 1/06; C07G 17/00; A61K 35/14; A61K 31/70
[52] U.S. Cl. ........................ 536/127; 536/53; 536/55.3; 526/209; 554/80; 554/83; 554/79; 554/191
[58] Field of Search ............ 536/127, 53, 55.3; 514/25, 823; 526/209; 530/387; 260/113

[56] References Cited

U.S. PATENT DOCUMENTS

| | | | |
|---|---|---|---|
| 3,687,927 | 8/1972 | Huber | 530/387 |
| 3,930,047 | 12/1975 | Dale et al. | 426/546 |
| 4,474,663 | 10/1984 | Nakajima et al. | 210/635 |
| 4,497,710 | 2/1985 | Wagu et al. | 210/635 |
| 4,521,593 | 6/1985 | Martin | 536/53 |
| 4,552,755 | 11/1985 | Ramden | 424/81 |
| 4,576,927 | 3/1986 | Kuroda et al. | 502/402 |
| 4,771,039 | 9/1988 | Tanaka et al. | 514/25 |
| 4,888,324 | 12/1989 | Catsimpoolas et al. | 514/25 |

FOREIGN PATENT DOCUMENTS 2915614  10/1990  Fed. Rep. of Germany .

OTHER PUBLICATIONS

Schott, et al., "A Dihydroxyboryl-Substituted Methacrylic Polymer for the Column Chromatographic Separation of Mononucleotides, Oligonucleotides, and Transfer Ribonucleic Acid" Biochemistry, vol. 12, No. 5, pp. 932-988 (1973).

Aldrich Technical Information Bulletin No. AL-102 (Sep. 1978).

Wertz et al; (Abstract) J. Lipid Res; Nov. 1985, 26(11) pp. 1333-1337.

*Primary Examiner*—Michael G. Wityshyn
*Assistant Examiner*—Louise N. Leary
*Attorney, Agent, or Firm*—Vogt & O'Donnell

[57] ABSTRACT

Glycolipids and phospholipids are obtained by dissolving a mixture of complex lipids in a solvent to form a solution and then passing the solution over a boric acid gel. Glycolipids are retained in the gel, and phospholipids are eluted through the gel.

16 Claims, No Drawings

PROCESS FOR OBTAINING GLYCOLIPIDS AND PHOSPHOLIPIDS

BACKGROUND OF THE INVENTION

This invention relates to a method for the separation of glycolipids from a lipid mixture containing complex lipids (CLS).

Complex lipids are chemical structures that are widespread in biological tissues where they occupy a fundamental position in the intermediate metabolism and in the cells of certain organs, such as the brain and the liver. They are divided into two main classes, namely: the phospholipids (PLS) which give mineral phosphates by hydrolysis, for example phosphatidyl choline (PC), phosphatidyl ethanolamine (PE), phosphatidyl inositol (PI); and the glycolipids (GLS) of which the structural bases sphingosine, for example the cerebrosides, hematosides, gangliosides, glycerol, for example the mono- and digalactosyl diglycerides, or sterols, for example the steryl glucosides and their esters, contain at least one sugar residue. The quantity of (GLS) in the CLS is generally 3 to 10 times smaller than that of the PLS.

The animal GLS, which are present in high concentrations in the brain, constitute important functional components of the membranes and are involved in the intramembranal transport, cell recognition, synaptic transmission, cell growth, hormone fixation, enzymes, bacteria, bacterial toxins, malignant tranformations and in many other biological functions. The GLS are thus used, for example, in medicine, in pharmacology, in geriatrics and in cosmetics.

It is known that GLS can be completely or partly extracted from biological tissues by means of various mixtures of polar organic solvents, for example chloroform-methanol, hexane-isopropanol, tetrahydrofuran-water. In these processes, they are only obtained in admixture with the neutral lipids (NLS) and the PLS so that these extracts are called total lipids (TLS). Alternatively, the biological tissues are first extracted with acetone to eliminate a large part of the NLS, for example the triglycerides, sterols and free fatty acids, after which the residual membranal lipids are extracted with the polar organic solvents mentioned above. The TLS may continue to be separated in various ways. The most widely used method is the Folch process which comprises collecting, in a two-phase solvent system of chloroform, methanol and water, an upper phase containing the majority of gangliosides, the GLS containing more than 4 to 5 sugar residues and traces of acidic PLS (APLS) and a lower phase containing the majority of the PLS, the ceramides, the steryl glucosides, the ceramides mono-, di- and trihexosides and all the non-polar lipids, for example the triglycerides. However, the separation of the lipids is not clean so that, for example, hematosides are found in the two phases.

One known large-scale method for separation of the NLS and CLS is based on the use of a mixture of hexane and ethanol. Other methods use liquid chromatography, but are attended by the disadvantage of inadequate capacity, for example 30 mg lipids per g silica gel. A very attractive process which is described in patent application DE 2 915 614 comprises separating the TLS into NLS and PLS on silica gel, although there is no mention of the other CLS, such as the gangliosides or the GLS. In this process, the NLS are defined as that part of the TLS which is soluble in hydrocarbons, as opposed to the PLS which form micelles in those solvents. Only the lipids which form micelles are freely eluted from the silica gel while the NLS remain adsorbed.

However, this process is attended by disadvantages. In fact, many GLS do not spontaneously form micelles in the presence of hydrocarbons. As a result, solid particles insoluble in the hydrocarbons are formed and obstruct the column of silica gel which thus adsorbs the NLS. Accordingly, only the PLS are quantitatively eluted from the column.

Although complete recovery of the GLS from the CL mixtures is possible, it takes an unusually long time. In the standard method, the lipids are first completely dried for 24 to 48 h over phosphorus pentoxide and then acetylated with acetic anhydride in pyridine. The acetylated GLS are then separated from the other lipids by liquid chromatography in a column of Florisil, the GLS are deacetylated and neutralized, the salts are eliminated and, finally, the product is dried by freeze-drying. The method is destructive to all the PLS and to certain GLS containing bonds sensitive to bases, for example the gangliosides with N-O-diacetyl neuraminic acid. In addition, the operation takes several days or even a whole week.

It has been proposed to resolve the difficulties discussed in the foregoing by a simple method of liquid chromatography comprising preparing a reuseable resin containing phenylboronic acid (PBA) groups fixed by covalent bonding to a matrix of crosslinked polystyrene. The resin selectively retains all the GLS by the formation of a complex between the PBA groups and the cis-diol groups of the sugar part of the GLS, thus providing for complete elution of the PLS and NLS. The GLS are then decomplexed with an aqueous organic solvent. However, the charging capacity of the resin is relatively low, typically 0.7 to 7 mg TL per g or 0.18 to 1.8 mg per ml resin (apparent volume). The volume of elution solvent required for 1 mg TL is of the order of 2.5 to 25 ml. It has been found that the commercially available resin cartridges containing 100 mg resin are ineffective for separating the PLS and GLS.

SUMMARY OF THE INVENTION

It has been found that the GLS can be separated substantially quantitatively from a lipid mixture containing CLS by a simple chromatographic method which is not destructive to the PLS.

The process according to the invention is characterized in that the mixture is dissolved in an appropriate solvent and passed over a boric acid gel so that the glycolipids are selectively adsorbed, after which the glycolipids are desorbed from the gel with an elution solvent.

DETAILED DESCRIPTION OF THE INVENTION

According to he invention, the lipid mixture used may be of animal or vegetable origin. Suitable animal lipids are those emanating from the solvent extraction of animal tissues available from abattoirs, such as for example intestines, lungs, thymus, bone marrow and, preferably, bovine brain. Another interesting starting material is human or animal placenta. These tissues may be in their natural, frozen or dehydrated state. Another interesting starting material available in large quantities is sweet buttermilk free from casein and lactose. Vegetable lipids are, for example, the natural soya lecithins.

To extract the lipids from the starting material, the starting material is disintegrated and homogenized, for example in a high-speed mill in a lipophilic, but water-miscible solvent or solvent mixture. For example, it is possible to use tetrahydrofuran, a mixture of tetrahydrofuran and water in a ratio by volume of 4:1 to 10:1, a mixture of diisopropyl ether and isopropanol in a ratio by volume of 3:2, chlorinated solvents, for example chloroform, dichloromethane, a mixture of chloroform and methanol in a ratio by volume of 2:1. It is of course possible to use similar lipophilic solvents and mixtures thereof. The operation is preferably carried out with heating to a temperature below 100° C., for example in the range from 50° to 60° C. The dispersion is then filtered and, after removal of the solvents, for example by distillation in vacuo to dryness, the crude TLS are collected. The crude TLS may optionally be purified by redissolving them in a solvent and then decanting and separating the solid particles deposited.

In an alternative procedure, the lipids may be extracted with a non-polar hydrocarbon solvent, for example hexane, which is preferred in the case of a starting material consisting of animal tissues dried by freeze-drying or spray-drying. In this case, the tissues are completely homogenized in a disintegration mill, for example in the presence of hexane at ambient temperature, after which extraction of the TLS is continued with stirring, for example at 60° to 62° C., in a closed stirrer-equipped reactor. The suspension is then left standing at ambient temperature for 1 to 2 h. A sediment is formed and, after separation from the supernatant phase, is retreated with a non-polar hydrocarbon, for example hexane as mentioned above. The combined supernatant phases may then be centrifuged in a centrifuge or, alternatively, are left standing for 24 to 48 h at ambient temperature. The sediment formed is separated and the clear solution is concentrated to approximately 12 to 15% of its initial weight, for example by evaporation in vacuo. The concentrate of TLS may be treated by dilution in an equal volume of distilled water, after which the residual hexane is eliminated, for example by evaporation under nitrogen at 68° to 70° C., and the aqueous emulsion is dried, for example by freeze-drying. Alternatively, the TL concentrate dissolved in hexane may be directly used as intermediate product in the preparation of the CLS by chromatography as described below. In this case, the eluate containing the CLS is concentrated to 5 to 10% of its initial volume after elimination of the solvent, after which it is diluted with an equal volume of distilled water and the emulsion is dried, for example by freeze-drying.

The lipid mixture may contain all the lipids, i.e. the NLS and the CLS, or preferably may be formed solely by the CLS. In this case, the CLS are separated beforehand in a column of silica gel in a non-polar, water-immiscible hydrocarbon solvent, for example petroleum ether, which serves as elution solvent for the CLS, the NLS remaining in the column. During dissolution of the lipids, sonication is preferably used in order to dissolve them completely. The CLS collected comprise in particular the PLS, the plasmalogens, the ceramide hexosides, the glyceroglycolipids and the gangliosides. The NLS are desorbed from the column using a polar, lipophilic solvent mixture, for example a mixture of chloroform and methanol. The NLS collected comprise in particular the mono-, di- and triglycerides, the fatty acids, the tocopherols, the liposoluble vitamins, the oestrogens and the phytooestrogens. It can be seen that the NLS do not contain any GLS, which is an advantage when it is desired to collect the fatty acids and the triglycerides containing these fatty acids free from GLS, particularly arachidonic acid, dihomogammalinolenic acid, eicosapentaenoic acid and docosahexaenoic acid, which are present in human placenta. After separation, the solvents are eliminated to dryness, for example by evaporation in vacuo.

In one variant of the preparation of the lipid mixture containing only the CLS, which is applicable in particular to the treatment of the lipids of buttermilk, the sweet (non-acidic) buttermilk freed from casein and lactose is treated, for example, by diafiltration (ultrafiltration with washing) with a polar solvent, for example acetone, to separate the NLS which pass into solution, after which the residue from which the acetone has been eliminated is treated with a slightly polar solvent, for example methanol, and the solution is then concentrated, for example by evaporation of the methanol. The concentrate obtained may be treated in a column of silica gel, as described above.

In a preferred variant of the treatment of the lipids of buttermilk, the TLS are extracted from the buttermilk freed from lactose and casein with a slightly polar solvent, for example with a mixture of hexane and methanol, and after separation of the residue, for example by microfiltration or centrifugation, the solvent mixture is eliminated, for example by evaporation. The TL concentrate is then treated with a polar solvent, for example acetone, in a distinctly smaller quantity than in the preceding variant where the buttermilk is directly treated. The insoluble fraction is collected and the acetone is eliminated therefrom. This pre-separation variant has several advantages over the preceding variant: the quantity of acetone required is approximately 10 to 12 times smaller; the material insoluble in acetone contains approximately 75 to 80% by weight CLS and only about 20 to 25% by weight NLS consisting of triglycerides of high melting point, which requires up to 15 times less silica gel than in the preceding case to achieve subsequent separation of the CLS. Finally, the material soluble in acetone, representing about 40 to 45% by weight of the buttermilk used, comprises—in addition to the triglycerides—the free fatty acids, the sterols and the majority of odour-emitting compounds which may thus be eliminated more easily. After this pre-separation, the lipid mixture obtained is treated by chromatography on silica gel, as described above.

A column filled with boric acid gel is used for separating the PLS from the GLS. The adsorbent is a crosslinked polymer insoluble in water and organic solvents. It is obtained by copolymerization and crosslinking of dihydroxyborylanilinomethacrylic acid and 1,4-butanediol dimethacrylate. Without wishing to limit ourselves to any one theory, it appears that the substantially quantitative separation of the PLS and GLS is due to the ability of the adsorbent to form complexes with the glycolipids by complexing the cis-diols of the GLS with the dihydroxyboryl groups of the gel and decomplexing in the presence of water. The boric acid gel is suspended in an anhydrous lipophilic solvent of medium polarity. For example, it is possible to use a mixture of chloroform and methanol in a ratio by volume of 5:1 to 2:1 or a mixture of diisopropyl ether and isopropanol in a ratio by volume of 4:2 to 2:1.

As mentioned above, the PLS are eluted from the column while the GLS are adsorbed. The PLS are collected using the same elution solvent, for example the mixture of chloroform and methanol in a ratio by volume of 2:1, after which the solvents are eliminated by evaporation in vacuo to dryness. The GLS are desorbed from the column using a solvent mixture comprising a polar, water-miscible organic solvent and 1 to 25% by weight deionized water. For example, it is possible to use a mixture of tetrahydrofuran and water in a ratio by volume of 10:1 to 4:1, a mixture of tetrahydrofuran, methanol and water, a mixture of chloroform, methanol and water, or a mixture of dichloromethane, methanol or ethanol and water. A mixture of tetrahydrofuran and water is preferably used. The proportions of the mixture may be varied during the elution process. For example, it is possible to start with a mixture rich in organic solvent, typically 10:1 by volume, and to finish with a 4:1 (by volume) mixture. The tetrahydrofuran has the advantage that it can be readily eliminated at the same time as the water, for example during subsequent freeze-drying. If a mixture containing an alcohol is used, only the GLS soluble in the alcohol/water mixture will be desorbed and, in addition, the column will have to be washed with a mixture of tetrahydrofuran and water during regeneration.

In certain cases, fine separation of the GLS is required. To this end, the GLS are dissolved in a solvent mixture of chloroform and methanol, for example in a double-walled stirrer-equipped decantation flask heated for example to 50° C., into which an aqueous solution of KCl is introduced. Initially, stirring is rapid, but then slowed down. Two phases are formed, namely an aqueous phase containing the gangliosides and an organic phase containing the other GLS. After separation of the lower phase, for example by gravity drainage, the solvents are eliminated therefrom, for example by evaporation in vacuo.

In one particular embodiment of the process according to the invention, the PLS may be separated into non-acidic PLS (NPLS) and acidic PLS (APLS) on the one hand while the GLS may be separated into non-acidic GLS (NGLS) and acidic GLS (AGLS) on the other hand by ion exchange chromatography. The advantage of these subsequent separations is that the standard methods of analysis, such as high-performance liquid chromatography (HPLC), high-performance thin-layer chromatography (HPTLC) and nuclear magnetic resonance spectroscopy (NMR) do not allow the detection and quantitative determination of the various fractions of CLS, because the number of classes of lipids present in the biological extracts is far too high for these methods to be effective. Elution by HPLC of all the classes of lipids present cannot be achieved without using various mobile phases or without synthesizing derivatives of certain lipids. Pre-separation by crosslinked agarose ion exchanger resin, particularly on rapid-throughput diethylaminoethyl sepharose gel in acetate form, enables GLS and the PLS to be quantitatively separated into their various acidic and non-acidic fractions with throughputs of as high as 10 bed volumes per hour. By virtue of this separation, the various fractions may then be identified and quantified by HPTLC combined with fluorescence detection.

In another particular embodiment of the process according to the invention, the natural lecithins of soya may be treated, for example, without preliminary separation of the NLS and with substantially complete elimination of the GLS and the free sugars by passage over a boric acid gel. Subsequent dialysis of the fraction containing the GLS against deionized water enables the free sugars to be eliminated. Phytoglycolipids are thus obtained. In a variant of this embodiment, the NLS and CLS are preseparated on silica gel, after which the GLS and the PLS are separated from the CLS on boric acid gel. The PLS obtained are free from glycolipids and free sugars. Accordingly, they no longer involve any of the risks typical of PLS, for example in parenteral emulsions, and in this context their composition is comparable with that of egg lecithin.

The invention also relates to the use of the fractions emanating from the separations.

In a first embodiment, the PLS, GLS and gangliosides of animal tissues and the PLS of buttermilk may be used in the preparation of cosmetic compositions.

In a second embodiment, the PLS, GLS and gangliosides, of which the composition is specific for each tissue from which these fractions have been extracted, are used in the formulation of dietetic compositions intended in particular for infant nutrition.

In a third embodiment, the fractions containing the gangliosides may be used for the preparation of liposomes suitable for use in cosmetics or for the preparation of medicines for treatment of the nervous system.

In a fourth embodiment, the soya lecithins free from phytoglycolipids may be used in the preparation of parenteral emulsions.

In a final embodiment, the NLS of human placenta may be used to obtain fatty acid triglycerides free from GLS containing in particular arachidonic, dihomogammalinolenic, eicosapentaenoic and docosahexaenoic acids. These triglycerides may be used in conjunction with other fractions obtained in accordance with the invention, particularly the PLS, GLS and gangliosides, for the preparation of dietetic compositions intended in particular for infant nutrition.

EXAMPLES

The invention is illustrated by the following Examples in which the parts and percentages are by weight, unless otherwise indicated.

In these Examples, the effectiveness of the separation of the NLS and CLS by HPTLC from samples was tested on plates of glass measuring 10×10 cm covered with silica gel. The various constituents of the fractions were detected by fluorescence in comparison with standard, well-defined compounds.

The quantitative separation of the GLS from the CLS was determined by several methods: HPTLC, colorimetry and gas-phase chromatography (GLC). In particular, the separation of the glycolipids by HPTLC was determined by detection with orcinol which specifically colours the sugar groups of the glycolipids by comparison with standard pure GLS.

To analyse the PL fraction, the PLS were preseparated into NPLS and APLS by ion exchange chromatography, followed by detection of the various components by HPTLC of each fraction by comparison with standard pure PLS.

At the same time, the contents of the GL fraction were verified by preliminary ion exchange chromatography, followed by analysis of the various non-acidic components (NGLS) and acidic components (AGLS) by HPTLC by comparison with standard samples.

EXAMPLE 1

1.1 Extraction of the TLS of bovine brain 5 kg bovine brain in the form of a powder dried by spray drying are homogenized in 50 l of a solvent mixture of tetrahydrofuran and water (ratio 4:1 by volume) at 20° C. in a rotary mixer rotating at 10,000 r.p.m.

After 3 to 5 minutes, extraction of the cerebral lipids is continued for 20 minutes at 50° to 60° C. in a 100 liter closed reactor with stirring at 160 to 250 r.p.m. The suspension obtained is passed through a double-jacketed filtration tank at 40° to 50° C. equipped with a one-stage paper filter. The solid particles retained in the filtration tank are removed with 35 l of a mixture of tetrahydrofuran and water in a ratio by volume of 4:1, the solvent being kept at a temperature of 40° to 50° C. The combined filtrates containing the crude cerebral lipid extract are then concentrated to constant weight in a vacuum evaporator at 65° to 75° C., after which the residual water is eliminated from the lipid concentrate by successive additions of 5 l isopropanol each followed by azeotropic evaporation.

1.2 Purification of the crude lipids

The preceding crude extract representing 2.68 kg is redissolved in 10 l tetrahydrofuran and then centrifuged for 10 minutes at 1500 to 1700 g in bottles closed by capsules. Alternatively, the dissolved crude extract is left standing for 24 h at ambient temperature, after which the solids deposited are separated. The clarified solution is concentrated to dryness at 65° to 70° C. in a rotary vacuum evaporator. 2.32 kg cerebral TLS and 0.36 kg non-lipid impurities are obtained.

1.3 Isolation of the CLS of bovine brain

A 100 cm long glass column with an internal diameter of 21.3 cm containing 15 l petroleum ether at 60° to 80° C. is filled with 4 kg 0.21–0.062 mm (70–230 mesh) silica gel particles dispersed in 20 l petroleum ether. The silica gel was activated beforehand by treatment for at least 16 h at 160° to 165° C. The glass column comprises a filter of fritted glass having a porosity of 100 to 160 microns to retain the particles of silica gel. The preceding cerebral TLS, i.e. 2.32 kg, are dissolved by stirring in 10 l petroleum ether and then sonicated for 2 to 5 minutes (250–500 W/kg lipids) until the cloudy solution becomes clear. The temperature of the sonicated sample is kept at 45° to 50° C. It is then passed through the column of silica gel and the CLS are completely eluted with 15 to 30 l petroleum ether (eluate 1). The NLS (eluate 2) are desorbed from the silica gel using 15 l of a mixture of chloroform and methanol in a ratio by volume of 1:1.

1.4 Regeneration of the silica gel adsorbent 15 l methanol and then 15 to 20 l deionized water are passed through the adsorbent. The adsorbent is then oven-dried for 6 h at 105° C. and then for 18 h at 160° to 165° C. Finally, the reactivated adsorbent is dispersed in 15 l petroleum ether to avoid any contact with atmospheric moisture.

1.5 Freeze drying of the CLS of bovine brain

The preceding eluate 1 is concentrated to complete dryness at 50° to 75° C. in a 50–100 l rotary vacuum evaporator. The CLS are then exposed to a stream of nitrogen for 12–24 h at ambient temperature to eliminate any residual trace of solvent. The lipids freed from their solvent are then homogenized in distilled water (5 kg water to 1 kg CLS) at 40° to 45° C., after which the emulsion obtained is spread in 1 to 1.5 cm thick layers over plates of stainless steel. The emulsion is then frozen at −40° C. and freeze-dried. 1.45 kg CLS are thus obtained.

1.6 Recovery of the NLS

The eluate 2 is concentrated to dryness as in paragraph 1.5. After elimination of the solvent as in 1.5, 0.48 kg NLS are obtained.

1.7 Separation of the PLS and GLS of bovine brain

The CLS of bovine brain prepared as described in 1.5 above are dissolved in a mixture of chloroform and methanol in a ratio by volume of 4:1 in a proportion of 1 g lipids to 5 g solvent mixture. Dissolution of the lipids is accelerated by sonication at 40° to 50° C., after which every particle is eliminated by passing the solution through a Büchner filter.

The glass adsorption column used, which is 30 cm long and has an internal diameter of 5 cm, comprises two bed supports of fritted glass having a porosity of 100 to 160 microns and a throughput adaptor enabling the height of the bed to be regulated from 15 to 30 cm. The column is connected to a low pressure (1–2 bar) pump which is capable of delivering three different elution solutions through a three-way valve at rates of 0 to 60 ml/min. 150 g boric acid gel is suspended in 1,000 ml tetrahydrofuran and the suspension is poured into the column in successive batches, any excess solvent being left to flow by gravity. The throughput adaptor is adjusted to the bed height of 20 to 22 cm. Before use, the column is washed with 3 bed volumes (1,200–1,300 ml) deionized water at a rate of 30 to 50 ml/min., then with 1 bed volume 0.5N hydrochloric acid, then with 3 bed volumes or more of deionized water to a neutral pH value, 3 bed volumes of methanol and, finally, 3 bed volumes of a mixture of chloroform and methanol in a ratio by volume of 2:1.

The column is prewashed with 20 ml of a mixture of chloroform and methanol in a ratio by volume of 4:1 at a rate of 20 ml/min. The column is then charged with the sample of CLS of bovine brain, i.e. 30 g lipids to 150 g of the mixture of chloroform and methanol in a ratio by volume of 4:1, at the same rate and then with 20 ml of a mixture of chloroform and methanol in a ratio by volume of 4:1. The PLS and the plasmalogens are eluted from the column using 3 bed volumes (1,200–1,300 ml) of a mixture of chloroform and methanol in a ratio by volume of 2:1 at a rate of 50 ml/minute. To elute all the GLS, comprising for example the ceramide hexosides, gangliosides and sulfatides, 3 bed volumes of a mixture of tetrahydrofuran and water in a ratio by volume of 4:1 are used at the same rate as for the PLS.

1.8 In-line regeneration of the column of boric acid gel

The column of boric acid gel is regenerated after each elution cycle using 3 bed volumes of a mixture of chloroform and methanol in a ratio by volume of 2:1 at a rate of 60 ml/min. to dehydrate the gel.

1.9 Isolation of the PLS and GLS of bovine brain

The fraction containing the PLS is concentrated to dryness in vacuo at 65° to 70° C. and then freeze-dried as described above (paragraph 1.5). 950–970 g of a white, hygroscopic powder free from any odour are thus obtained.

The fraction containing the GLS is concentrated in vacuo at 70° to 75° C. until the tetrahydrofuran is completely eliminated and the residue is taken up in deionized water to a volume of 2,500 ml. After homogenization, the emulsion containing the glycolipids is freeze-dried as described above. 480–490 g of an odourless white powder are obtained.

EXAMPLE 2

2.1 Extraction of the lipids of lactose-free buttermilk

Fresh buttermilk is freed from lactose by diafiltration and is then dried by spray-drying. The buttermilk powder obtained has the following composition:

| | % |
|---|---|
| Moisture (as measured after 2 h in an oven at 102° C.) | 2.5 |
| Fats (Mojonnier's method) | 52.9 |
| Proteins (N × 6.38) | 29.7 |
| Lactose (enzymatically determined) | 8.1 |
| Ash | 6.8 |

80 kg buttermilk powder are then dispersed in 450 l acetone at 20° to 22° C. using a homogenizer. The fats are extracted in a closed reactor equipped with a blade agitator rotating at 120 to 250 r.p.m. The extraction temperature is kept at 20° to 22° C. for about 20 minutes, after which the dispersion is filtered in a tank equipped with a one-stage paper filter. The solid particles retained are then washed with another 300 l acetone at 20° to 22° C. the combined filtrates are then dried by evaporation in vacuo and 26 kg neutral buttermilk lipids are collected. Nitrogen is then passed through the fat-free buttermilk residue retained in the filtration tank kept at 35° to 40° C. for 2 h to eliminate the solvent.

The 53–55 kg fat-free and solvent-free buttermilk solids are then dispersed in 560 l methanol in a homogenizer rotating at 10,000 r.p.m., after which extraction of the lipids is continued for 20 to 30 minutes at 60° to 62° C. in a double-walled reactor. The dispersion is then passed through a paper filter arranged in a closed double-walled tank at 60° to 62° C. under a pressure of 1.5 to 2.5 bar, after which the solid particles retained on the filter are removed with 80 l hot methanol. The methanolic filtrate is then concentrated to a volume of 40 to 45 l and the residual methanol is evaporated by azeotropic distillation with 100–150 l petroleum ether which forms an azeotropic mixture with the methanol between 60° and 90° C.

2.2 Isolation of the CLS of buttermilk

The volume of the preceding concentrate obtained in 2.1 is adjusted to 100 l with petroleum ether, after which the solution is left standing for 48 h at ambient temperature. Any solid deposits formed are eliminated by filtration, after which the clarified petroleum ether phase is passed through a 100 cm long column with an internal diameter of 35 cm containing 26 kg (corresponding to 1 bed volume of approximately 65 l) of silica gel, as described above in Example 1, paragraph 3. All the CLS are eluted with 65–70 l petroleum ether (eluate 1), while the adsorbed lipids are desorbed with 80 l of a mixture of chloroform and methanol in a ratio by volume of 1:1 (eluate 2). Eluate 1 is concentrated in vacuo to dryness, dispersed in deionized water and then freeze-dried as described in paragraph 5 of Example 1. 10.2 kg CLS are thus obtained. Eluate 2 concentrated to dryness gives 5.1 kg residual NLS.

2.3 Separation of the PLS and GLS of buttermilk

A sample of 600 g of CLS of buttermilk obtained as described in paragraph 2.2 above is passed through a column of boric acid gel and the PLS are separated from the GLS in the same way as described in paragraph 7 of Example 1. After concentration to dryness and freeze-drying, as described in paragraph 1.9 of Example 1, 365 g of PLS of buttermilk are obtained in the form of a whitish, odourless powder.

2.4 Purification of the GLS of buttermilk

The fraction containing the GLS is concentrated in vacuo in order completely to eliminate the tetrahydrofuran as described in paragraph 1.9 of Example 1, after which the residue is taken up with deionized water to a volume of 800 ml. The aqueous solution of GLS is then dialyzed against deionized water at 4° C. for 24 h using a dialysis membrane having a molecular weight cutoff limit of 3500 daltons. The solution of GLS is then freeze-dried, giving 160 g of a white powder of purified GLS containing less than 1% free lactose. After drying, the dialyzate represents 75 g.

EXAMPLE 3

3.1 Isolation of the CLS of ox bone marrow 10 kg freshly homogenized ox bone marrow are freeze-dried and the 1.6–1.7 kg dry matter obtained are dispersed in 50 l of a solvent mixture of dichloromethane and methanol in a ratio by volume of 2:1 at 20° to 22° C. The TLS of ox bone marrow are extracted in a closed reactor as in Example 1, paragraph 1. After filtration and elimination of the solvent mixture as in Example 1, paragraph 2, 0.65 kg TLS are obtained and are redissolved in 2.5 l hexane and the resulting solution is passed through a 40 cm long glass column with an internal diameter of 10 cm filled with 750 g silica gel, as described in Example 1.

The CLS are eluted with 2 l hexane while the NLS are desorbed from the column by passing 2 l of a mixture of chloroform and methanol in a ratio by volume of 2:1 through the column. The CLS are freeze-dried as described in Example 1, paragraph 5, giving 430 g of a white, hygroscopic, odourless powder.

3.2 Separation and isolation of the GLS and PLS of ox bone marrow

The above 430 g CLS of ox bone marrow are dissolved in 2,150 g of a solvent mixture of chloroform and methanol in a ratio by volume of 4:1, as in Example 1, paragraph 7. The CLS are separated into their PLS and GLS fractions, as described in 1.7, from 30 g lipids to 150 g solvent and the column of boric acid gel is regenerated after each cycle using 3 bed volumes of a mixture of chloroform and methanol in a ratio by volume of 2:1, as in 1.8. The eluted and desorbed fractions are then concentrated and freeze-dried as in 1.9, giving 274 g PLS and 150 g GLS in the form of odourless, white powders.

EXAMPLE 4

4.1 Separation by solvent of the GLS of bovine brain 60 g GLS of bovine brain prepared as in Example 1, paragraph 9, are dispersed in a solvent mixture consisting of 3,200 ml chloroform and 1,600 ml methanol in a 10 liter capacity, double-walled decantation flask equipped with a shaft stirrer in its upper part. The shaft of the stirrer is equipped with two blades spaced apart from one another so that only the lower blade is immersed in the solvent. The temperature of the solution of GLS is progressively increased to 50° C., after which 1,200 ml of an 88% aqueous KCl solution are added, thus submerging the upper blade of the stirrer. From an initial speed of 300 to 600 r.p.m., the stirrer is slowed down to 5-10 r.p.m. and the heating of the decantation flask is switched off after 15 minutes. Two phases are formed, each continuing to be agitated by one of the blades. After 8 to 12 h, complete separation of the gangliosides from the other GLS is observed when the upper aqueous phase containing gangliosides and the lower phase containing the other GLS become clear. The lower phase is allowed to flow from the decantation flask by gravity and the upper phase is separately collected. The other GLS in the lower phase are formed by monogalactosyl ceramides and sulfatides.

4.2 Isolation of the phases of GLS

The lower phase containing all the sulfatides and the neutral GLS (monogalactosyl ceramides) is concentrated to dryness in vacuo at 65° to 75° C. and then freeze-dried as described in Example 1, paragraph 9. The end product is a spotless white powder consisting of 49 g pure GLS (monogalactosyl ceramides and sulfatides). The upper phase is concentrated in vacuo at 65° to 70° C. to complete elimination of the organic solvents of which the initial volume is thus reduced by approximately 2,400 ml to 300-600 ml of a clear solution. The aqueous solution is then dialyzed as in Example 2, paragraph 4, after which the concentrated upper phase is freeze-dried as described in Example 1, paragraph 9. The end product is 5.1 g of an odourless, spotless white powder containing the gangliosides typical of bovine brain as listed in the following using the abbreviations of Svennerholm and Holmgren:

NeuAc$\alpha$2→3 Gal$\beta$1→3 GalNAc$\beta$1→4 [NeuAc$\alpha$2→3]Gal$\beta$1→Glc→Cer (GD1a), NeuAc$\alpha$2→8 NeuAc$\alpha$2→3 Gal$\beta$1→4Glc→Cer (GD3), NeuAc$\alpha$2→3 Gal$\beta$1→3 Gal NAc$\beta$1→4[NeuAc$\alpha$2→8 NeuAc$\alpha$2→3] Gal$\beta$1→4 Glc→Cer (GT1b) and Gal$\beta$1→3 Gal NAc$\beta$1→4 [NeuAc$\alpha$2→3] Gal$\beta$1→4 Glc→Cer (GM1).

EXAMPLE 5

Separation of the GLS of buttermilk

The GLS of buttermilk isolated as in Example 2, paragraph 4 are separated using the extraction process of Example 4. The upper phase containing the gangliosides is concentrated in vacuo at 65° to 70° C. until the organic solvents chloroform and methanol have been completely evaporated, the initial volume of approximately 2,400 ml being reduced to 300-600 ml. The aqueous concentrate is dialyzed for 24 h at 4° C. against deionized water as described in Example 2, paragraph 4. The end product is a spotless powder of 4.8 g consisting essentially of gangliosides typical of buttermilk, such as GD$_3$ (representing approximately 80%), GM$_1$ (explained in Example 4.2) and NeuAc $\alpha$ 2→3 Gal$\beta$1→4 Glc→Cer (GM3 according to Svennerholm and Holmgren). Its free lactose content is below 1%.

The lower phase is concentrated to complete dryness and then freeze-dried as in Example 4, paragraph 2. 46 g of a spotless white powder are obtained, containing only neutral glycolipids, such as the dihexosyl and trihexosyl ceramides, and no free lactose.

EXAMPLE 6

6.1 Separation of the CLS of human placenta

Human placenta is extracted with a solvent mixture of isopropyl ether and isopropanol in a ratio by volume of 3:2 and is then sonicated in hexane at 55° to 60° C. (400 W/100 g placenta in 350 ml hexane) until the initially cloudy solution becomes clear. A 30 cm glass column with an internal diameter of 5.5 cm equipped with a filter of fritted glass is filled with 100 g 0.21-0.062 mm (70-230 mesh) silica gel particles activated beforehand for 15 h at 160°-165° C. and then dispersed in hexane.

The sample is then passed through the column at 50° C., after which elution of the CLS is completed with 400 to 500 ml hexane (eluate 1).

The NLS (eluate 2) are desorbed from the column using 500 ml of a solvent mixture of chloroform and methanol in a ratio by volume of 1:1. Concentration of eluates 1 and 2 to dryness in vacuo gives 55.3 g CLS and 44.7 g NLS.

The fraction containing the CLS has the advantage of not comprising the oestrogens which generally accompany the CLS when the conventional methods of extraction and separation based on solvent mixtures are used.

To regenerate the column, 250 ml methanol and then 1,000 ml deionized water are passed through the adsorbent, followed by thermal activation as described above.

6.2 Isolation of the PLS and GLS of human placenta

A 30 cm long glass column with an internal diameter of 5.5 cm equipped with a filter of fritted glass is filled with 100 g boric acid gel. The gel suspended in a solvent mixture of chloroform and methanol in a ratio by volume of 2:1 is covered with an approximately 1 cm thick layer of quartz sand. The adsorbent is then successively washed with 3 bed volumes methanol, 3 bed volumes deionized water, 1 bed volume 0.5N HCl solution and then 10 bed volumes deionized water to the neutral pH value and the gel is converted into lipophilic form using 3 bed volumes methanol and then 3 bed volumes of a solvent mixture of chloroform and methanol in a ratio by volume of 2:1.

15 g CLS of human placenta obtained as described in 6.1, dissolved in 60 ml of a solvent mixture of chloroform and methanol in a ratio by volume of 2:1, are passed through the column. After concentration of the eluate in vacuo to dryness, 14 g PLS (eluate 1) are obtained. The GLS (eluate 2) are desorbed from the column using 600 ml of a solvent mixture of tetrahydrofuran and water in a ratio by volume of 4:1. After regeneration of the column with 600 ml of a mixture of chloroform and methanol in a ratio by volume of 2:1, followed by passage of a second sample of 15 g CLS of human placenta, regeneration of the column and, finally, passage of a third sample of 15 g CLS of human placenta, the fractions of PLS (eluate 1) are combined, the solvents are eliminated to complete dryness and 40 to 42 g PLS of human placenta are collected. After combined eluates 2 containing the GLS have been concentrated to dryness, the residue is resuspended in water by sonication at 50° C. and, after freeze-drying, 3 g GLS of human placenta are collected.

EXAMPLE 7

Isolation of the phytoglycolipids of soya 25 g commercially available natural soya lecithin are dissolved in 75 ml of a solvent mixture of chloroform and methanol in a ratio by volume of 4:1 and the resulting solution is passed through a column of boric acid gel as described in Example 6, paragraph 2. This gives 22.7 g of a mixture of NLS and PLS and 2.3 g of a fraction containing the phytoglycolipids and the free sugars. Dialysis and concentration as in Example 2, paragraph 4, give 1 g (4%) of soya phytoglycolipids free from free sugars.

EXAMPLE 8

Separation of the PLS and phytoglycolipids of soya

A 40 g fraction containing the NLS and a 60 g fraction containing the CLS are separated from 100 g commercially available natural soya lecithin as in Example 1, paragraph 3.

The fraction containing the CLS is redissolved by sonication at 40° C. in 200 ml of a solvent mixture of diisopropyl ether and isopropanol in a ratio by volume of 3:2 and the resulting solution is passed in successive batches of 15 g through a column—30 cm long with an internal diameter of 5.5 cm—of boric acid gel dispersed in a solvent mixture of diisopropyl ether and isopropanol. The fractions containing the PLS are eluted using 2 bed volumes of a solvent mixture of diisopropyl ether and isopropanol in a ratio by volume of 3:2 and then 1 bed volume of isopropanol.

The fractions containing the phytoglycolipids are desorbed from the column with 3 bed volumes of a solvent mixture of tetrahydrofuran and water in a ratio by volume of 4:1, as described in Example 6, paragraph 2. After each cycle, the adsorbent is regenerated using 1 bed volume of isopropanol and then 2 bed volumes of a solvent mixture of diisopropyl ether and isopropanol in a ratio by volume of 3:2.

The combined fractions of PLS on the one hand and phytoglycolipids on the other hand are separately collected and concentrated to dryness in vacuo, 40 g PLS and 20 g phytoglycolipids being obtained.

The PLS thus prepared are remarkable in that they are free from the compounds naturally present in soya lecithins which can cause undesirable secondary effects.

They are comparable with those of egg yolk lecithin which are poor in glycolipids and free sugars, making them attractive for the preparation of parenteral emulsions well tolerated by the human organism.

EXAMPLE 9

9.1 Separation of the PLS and GLS of guinea-pig intestine 7.86 g guinea-pig intestines are successively washed in 2×80 ml of a solvent mixture of chloroform and methanol in a ratio by volume of 1:2, the homogenizate is centrifuged at 2500 g and the clear supernatant liquid is concentrated in vacuo to dryness.

The 290 mg crude lipids obtained are dissolved by sonication in 10 ml tetrahydrofuran, the solution is centrifuged at 2500 g and then concentrated to dryness to obtain 250 mg TLS. The NLS are eliminated as the sterols, free fatty acids and triglycerides by dissolving the TLS by sonication in 2×2.5 ml hexane and by passing the solution through a 10 cm long glass column with an internal diameter of 1 cm filled with 0.21–0.062 mm (70–230 mesh) particles of activated silica gel. 190 mg CLS are thus quantitatively eluted with 25 ml hexane. 57 mg NLS are desorbed from the column with 3 bed volumes of a solvent mixture of chloroform and methanol in a ratio by volume of 2:1. The CLS are then separated into 143 mg PLS and 47 mg GLS, as described above in Example 1, paragraph 7. Dialysis against deionized water and lyophilization gives 16.6 mg of a fraction of pure GLS with no free sugars.

9.2 Separation of the PLS of guinea-pig intestine into NPLS and APLS by ion exchange 8.5 ml rapid-throughput diethylaminoethyl sepharose gel are suspended in ethanol and a 10 cm long glass column with an internal diameter of 1.15 cm is filled with the resulting suspension. The gel is then washed with 30 ml deionized water, converted into acetate form with 20 ml of a 2M aqueous sodium acetate solution and washed successively with 30 ml deionized water, 10 ml methanol and, finally, 10 ml of a solvent mixture of chloroform and methanol in a ratio by volume of 2:1. The gel is covered with a 7 to 10 mm thick layer of quartz sand. The sample of 143 mg PLS of guinea-pig intestine is passed through the column, after which the non-acidic PLS are eluted with successive portions of 2×2 ml and then 10 ml of a solvent mixture of chloroform and methanol in a ratio by volume of 2:1 and, finally, 5 ml methanol. A slight pressure is maintained to accelerate elution. Elimination of the solvents in vacuo to dryness leaves 107 mg NPLS.

To desorb the acidic PLS retained on the column, 15 ml of a solvent mixture of chloroform, methanol and 0.8M aqueous sodium acetate solution (30:60:8) are passed through the column. After concentration of the acidic fraction to dryness and redissolution thereof by sonication in 2×1 ml of a solvent mixture of chloroform and methanol in a ratio by volume of 2:1, the salts are eliminated in a 10 cm long glass column with an internal diameter of 1.15 cm filled with 4 ml Sephadex G-25 gel in a solvent mixture of chloroform, methanol and water in a ratio by volume of 60:30:4.5, the column being maintained under a slight pressure. Elimination of the solvents in vacuo to dryness leaves 35 mg APLS. After each cycle, the ion exchange column is regenerated using 1 bed volume methanol and then 2 bed volumes of a solvent mixture of chloroform and methanol in a ratio by volume of 2:1.

The NPL fraction typically comprises phosphatidyl choline, phosphatidyl ethanolamine and sphingomyeline.

The APL fraction typically comprises phosphatidyl inositol, phosphatidyl serine, phosphatidic acid and cardiolipin.

9.3 Separation of the GLS of guinea-pig intestine into NGLS and AGLS

The NGL and AGL fractions are separated by the method described in pargraph 9.2 above. 11.9 mg NGLS and 4.5 mg AGLS are obtained from the preceding 16.6 mg (paragraph 9.1).

The NGLS obtained are typically ceramide hexosides and glycoglycerolipids.

The AGLS obtained are typically sulfatized, hematosides and gangliosides.

EXAMPLE 10

10.1 Variant of the extraction of the TLS of bovine brain 8 kg bovine brain in the form of a powder dried by spray drying are homogenized at ambient temperature in 45 kg hexane in a colloid mill, after which extraction is continued at 60° C. in a closed reactor equipped with blade stirrers rotating at 250 r.p.m.

After extraction for 30 minutes, the suspension is left standing for 1–2 h in a separate vessel. The supernatant phase is collected by decantation and the solids which have sedimented are reextracted with another 30 kg hexane.

The second extract is left standing for 1 to 2 h, the supernatant phase is collected by decantation and is then combined with the preceding supernatant phase. After standing for 24–48 h at ambient temperature, the combined supernatant phases give a translucent liquid phase from which a solid residue is separated by careful decantation.

The liquid phase is then preconcentrated at 66°-70° C. to 12-15% of its initial volume by evaporation in vacuo, after which the preconcentrate is diluted with an equal volume of distilled water. The solvent is eliminated by distillation at 68°-70° C. and the emulsion obtained is homogenized, frozen to −40° C. and then freeze-dried. 3.32 kg TLS of bovine brain are thus obtained in the form of an odourless, hygroscopic beige powder having the following composition:

|  | % |
|---|---|
| Cholestrol | 25-27 |
| CLS including | 73-75 |
| PLS | 50-53 |
| GLS including | 20-23 |
| neutral GLS and sulfatides | 15-18 |
| Gangliosides | 1.5-1.8 |

10.2 Variant of the separation of the CLS and NLS of bovine brain 8 kg powder-form bovine brain are treated as described in 10.1 above up to preconcentration of the liquid phase. The concentrate in hexane contains 3.3 kg TLS. A fine dispersion is prepared by sonication and is then passed through a column similar to that described in Example 1, paragraph 3, filled with 3.3-3.5 kg silica gel. The CLS are then eluted from the column with 20-25 l hexane and the eluate is preconcentrated to 12-15% of its initial weight by evaporation of the hexane in vacuo. After dilution with the same weight of water, the emulsion is treated as described in 10.1 above, giving 2.45 kg of CLS containing:

|  | % |
|---|---|
| PLS | 70-73 |
| GLS including | 25-28 |
| neutral GLS and sulfatides | 20-25 |
| Gangliosides | 2-3 |

The NLS are desorbed from the column with 2 bed volumes of a mixture of chloroform and methanol in a ratio by volume of 2:1, after which the eluate is concentrated to 5% of its own initial weight by evaporation in vacuo. After dilution with 5 l hexane, the solution of NLS is concentrated to dryness, giving 0.88 kg of a yellow powder containing more than 95% cholesterol.

EXAMPLE 11

11.1 Variation of the separation of the CLS of buttermilk

Sweet buttermilk is freed from casein and lactose by diafiltration and then dried by spray drying.

The buttermilk powder obtained has the following composition:

|  | % |
|---|---|
| Moisture (after 2 h in an oven at 102° C.) | 3.22 |
| Total solids, including | 96.78 |
| Total lipids (Mojonnier's method) | 61.24 |
| Proteins (N × 6.38) | 32.43 |
| Lactose (enzymatically determined) | 1.24 |
| Ash | 1.87 |

100 g of this powder are homogenized twice with 500 ml of a mixture of hexane and methanol in a ratio by volume of 94:6 for 1 minute at 50° C. in a colloid mill. After each homogenization, the homogenizate is centrifuged for 2 min. at 1,500 g.

The supernatant phase is then concentrated to dryness in vacuo at 65° C., giving 65.2 g of TLS which remain fluid by virtue of their high percentage of butter oil (70-75%).

The TLS are cooled to 40° C., homogenized with 1.5 to 2 times their volume of acetone (90-130 ml) in a colloid mill, left to return to ambient temperature (22°-24° C.) and then centrifuged for 1 minute at 2,000 g. The clear supernatant phase containing the majority of the NLS and odour-emitting compounds is eliminated. The solid residue collected contains the CLS. It is redissolved in hexane and then concentrated by evaporation in vacuo giving 21.7 g of a material insoluble in acetone (AIM).

This material is suspended in three times its volume of hexane, after which the CLS (80.6%) are separated from the NLS (19.4%) by liquid adsorption chromatography using an equivalent volume of silica gel (10-11 g).

The preceding CLS of buttermilk (17.5 g) are then homogenized in 10 times their volume of distilled water and the emulsion is freeze-dried.

11.2 Second variant of the separation of the CLS of buttermilk 7.84 kg buttermilk powder having the same composition as described in 11.1 are treated with stirring under reflux with 90 l of a solvent mixture of hexane and methanol in a ratio by volume of 94:6. After 15 minutes, the suspension obtained is cooled to 40° C. and then passed through a microfilter, after which the filter is washed with 10 l of a mixture of hexane and methanol in a ratio by volume of 94:6.

The filtrate is then concentrated to dryness at 65° C. by evaporation in vacuo, giving 4.57 kg TLS which are cooled to 40° C., homogenized with twice their volume of acetone (10 l) and left to cool to ambient temperature (22°-24° C).

After centrifugation for 1 to 3 minutes at 1,500 g, the clear supernatant phase containing the majority of the NLS and odour-emitting compounds is discarded and the material insoluble in acetone (AIM) is taken up in 10 l hexane and then concentrated to dryness by evaporation in vacuo. 1.52 kg AIM are thus obtained.

The AIM is taken up in 3 to 4 times its volume of hexane (6-7 l) and then separated into its CLS (1.16 kg) and its NLS (0.36 kg) by adsorption chromatography on silica gel using approximately 1 kg adsorbent. The eluate containing the CLS is collected and dried by evaporation in a stream of nitrogen. After homogenization for 5 minutes at 40° C. with 9 times its volume of distilled water, the emulsion is dried by freeze-drying.

I claim:

1. A process for separating glycolipids from phospholipids comprising dissolving complex lipids in a solvent to form a solution and then passing the solution over a gel of copolymerized and crosslinked dihydroxyborylanilinomethacrylic acid and 1,4-butanediol dimethacrylate so that glycolipids are adsorbed on the gel and phospholipids pass through the gel.

2. A process according to claim 1 wherein the gel is suspended in an anhydrous lipophilic solvent of medium polarity.

3. A process according to claim 2 wherein the anhydrous lipophilic solvent comprises a mixture of chloroform and methanol.

4. A process according to claim 2 wherein the anhydrous lipophilic solvent comprises a mixture of diisopropylether and isopropanol.

5. A process according to claim 1 further comprising collecting the phospholipids which pass through the gel.

6. A process according to claim 5 further comprising passing the collected phospholipids over an ion exchange resin to separate acidic phospholipids from non-acidic phospholipids.

7. A process according to claim 1 further comprising desorbing the glycolipids from the gel and collecting desorbed glycolipids.

8. A process according to claim 7 wherein the glycolipids are desorbed with an elution solvent mixture comprising a polar, water-immiscible organic solvent and from 1% to 25% by weight deionized water.

9. A process according to claim 8 wherein the elution solvent mixture comprises tetrahydrofuran and deionized water.

10. A process according to claim 7 further comprising passing the collected glycolipids over an ion exchange resin to separate acidic glycolipids from non-acidic glycolipids.

11. A process according to claim 7 further comprising extracting the collected glycolipids in an aqueous/organic solvent mixture, separating an aqueous phase and an organic phase, and eliminating aqueous solvent from the aqueous phase to obtain gangliosides.

12. A process according to claim 1 wherein the complex lipids are obtained by passing a mixture containing complex lipids and neutral lipids over a column of silica gel in a non-polar water-immiscible solvent so that neutral lipids remain in the column and complex lipids are eluted through the column and are collected.

13. A process according to claim 1 wherein the complex lipids are obtained by extracting lactose-free buttermilk with a solvent.

14. A process according to claim 1 wherein the complex lipids comprise a natural soya lecithin.

15. A process for obtaining glycolipids and phospholipids comprising treating lactose-free buttermilk with a polar solvent to obtain a solution containing neutral lipids and a residue containing complex lipids, eliminating the polar solvent from the residue, treating the residue with a slightly polar solvent to obtain a solution containing complex lipids, eliminating the slightly polar solvent to obtain a concentrate, eluting the concentrate through a column containing silica gel to separate complex lipids from remaining neutral lipids, passing the complex lipids over a gel of copolymerized and crosslinked dihydroxyborylanilinomethacrylic acid and 1,4-butanediol dimethacrylate so that glycolipids are adsorbed on the gel and phospholipids pass through the gel, and collecting phospholipids and glycolipids.

16. A process for obtaining glycolipids and phospholipids comprising treating lactose-free buttermilk with a slightly polar solvent to form a solution and a residue, separating the residue from the solution, eliminating solvent from the solution to obtain a concentrate, treating the concentrate with a polar solvent, collecting an insoluble fraction from the polar solvent, eliminating traces of polar solvent to obtain a concentrate, separating complex lipids from the concentrate by adsorption chromatography on silica gel, passing the complex lipids over a gel of copolymerized and crosslinked dihydroxyborylanilinomethacrylic acid and 1,4-butanediol dimethacrylate so that glycolipids are adsorbed on the gel and phospholipids pass through the gel, and collecting phospholipids and glycolipids.

* * * * *